(12) United States Patent
Mallaby

(10) Patent No.: US 9,174,025 B2
(45) Date of Patent: *Nov. 3, 2015

(54) RAPID EXCHANGE CATHETERS HAVING A SEALED GUIDEWIRE LUMEN AND METHODS OF MAKING THE SAME

(71) Applicant: BOSTON SCIENTIFIC SCIMED, INC., Maple Grove, MN (US)

(72) Inventor: Mark Mallaby, San Diego, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 173 days.

This patent is subject to a terminal disclaimer.

(21) Appl. No.: 13/858,642

(22) Filed: Apr. 8, 2013

(65) Prior Publication Data

US 2013/0190700 A1   Jul. 25, 2013

Related U.S. Application Data

(63) Continuation of application No. 10/945,578, filed on Sep. 21, 2004, now Pat. No. 8,414,527.

(51) Int. Cl.
*A61M 25/01* (2006.01)
*A61M 25/10* (2013.01)

(52) U.S. Cl.
CPC ........... *A61M 25/0169* (2013.01); *A61M 25/10* (2013.01); *A61M 25/1027* (2013.01); *A61M 25/1034* (2013.01); *A61M 2025/0183* (2013.01)

(58) Field of Classification Search
CPC . A61M 25/00; A61M 25/10; A61M 25/0169; A61M 2025/0183; A61M 2025/0047

USPC ..................... 604/103.04, 523, 527
See application file for complete search history.

(56) References Cited

U.S. PATENT DOCUMENTS

| | | |
|---|---|---|
| 5,061,273 A | 10/1991 | Yock et al. |
| 5,135,494 A | 8/1992 | Engelson et al. |
| 5,135,535 A | 8/1992 | Kramer et al. |
| 5,209,728 A | 5/1993 | Kraus et al. |
| 5,290,241 A | 3/1994 | Kraus et al. |
| 5,290,247 A | 3/1994 | Crittenden et al. |
| 5,300,085 A | 4/1994 | Yock et al. |
| 5,306,247 A | 4/1994 | Pfenninger |
| 5,320,613 A | 6/1994 | Houge et al. |
| 5,324,259 A | 6/1994 | Taylor et al. |
| 5,324,269 A | 6/1994 | Miraki et al. |
| 5,328,472 A | 7/1994 | Steinke et al. |

(Continued)

OTHER PUBLICATIONS

U.S. Appl. No. 10/653,375, filed Sep. 2, 2003.

(Continued)

*Primary Examiner* — Laura Bouchelle
(74) *Attorney, Agent, or Firm* — Seager, Tufte & Wickhem LLP

(57) ABSTRACT

Methods and devices for preventing fluid flow through the relatively short guidewire lumen of a rapid exchange catheter. The guidewire lumen for a rapid exchange catheter is provided with a narrowed or sealed section allowing for passage of a guidewire therethrough while preventing fluid flow while a guidewire is disposed therethrough. The narrowed or sealed section extends for a relatively short length of the guidewire lumen to avoid creating excessive friction between the guidewire and the guidewire lumen. In several embodiments the narrowed or sealed section is placed proximal of the distal end of the guidewire lumen.

18 Claims, 4 Drawing Sheets

(56) References Cited

U.S. PATENT DOCUMENTS

| | | |
|---|---|---|
| 5,336,184 A | 8/1994 | Teirstein et al. |
| 5,346,505 A | 9/1994 | Leopold et al. |
| 5,348,537 A | 9/1994 | Wiesner et al. |
| 5,350,395 A | 9/1994 | Yock et al. |
| 5,364,354 A | 11/1994 | Walker et al. |
| 5,364,376 A | 11/1994 | Horzewski et al. |
| 5,389,087 A | 2/1995 | Miraki et al. |
| 5,395,332 A | 3/1995 | Ressemann et al. |
| 5,410,979 A | 5/1995 | Allen et al. |
| 5,425,712 A | 6/1995 | Goodin |
| 5,451,233 A | 9/1995 | Yock et al. |
| 5,454,788 A | 10/1995 | Walker et al. |
| 5,468,225 A | 11/1995 | Teirstein et al. |
| 5,470,315 A | 11/1995 | Adams et al. |
| 5,472,425 A | 12/1995 | Teirstein |
| 5,490,837 A | 2/1996 | Blaeser et al. |
| 5,501,227 A | 3/1996 | Yock et al. |
| 5,516,336 A | 5/1996 | McInnes et al. |
| 5,520,645 A | 5/1996 | Imran et al. |
| 5,522,818 A | 6/1996 | Keith et al. |
| 5,527,282 A | 6/1996 | Segal |
| 5,569,184 A | 10/1996 | Crocker et al. |
| 5,571,087 A | 11/1996 | Ressemann et al. |
| 5,598,844 A | 2/1997 | Diaz |
| 5,645,533 A | 7/1997 | Blaeser et al. |
| 5,667,493 A | 9/1997 | Janacek et al. |
| 5,690,613 A | 11/1997 | Verbeek |
| 5,693,015 A | 12/1997 | Walker et al. |
| 5,695,468 A | 12/1997 | Lafontaine et al. |
| 5,695,469 A | 12/1997 | Segal |
| 5,702,439 A | 12/1997 | Keith et al. |
| 5,718,680 A | 2/1998 | Kraus et al. |
| 5,720,724 A | 2/1998 | Ressemann et al. |
| 5,776,099 A | 7/1998 | Tremulis |
| 5,779,671 A | 7/1998 | Ressemann et al. |
| 5,785,658 A | 7/1998 | Benaron et al. |
| 5,807,355 A | 9/1998 | Ramzipoor et al. |
| 5,820,594 A | 10/1998 | Fontirroche et al. |
| 5,823,995 A | 10/1998 | Fitzmaurice et al. |
| 5,833,706 A | 11/1998 | St. Germain et al. |
| 5,849,016 A | 12/1998 | Suhr |
| 5,882,336 A | 3/1999 | Janacek et al. |
| 5,891,110 A | 4/1999 | Larson et al. |
| 5,921,958 A | 7/1999 | Ressemann et al. |
| 5,941,871 A | 8/1999 | Adams et al. |
| 5,947,927 A | 9/1999 | Mertens |
| 5,957,930 A | 9/1999 | Vrba et al. |
| 5,980,486 A | 11/1999 | Enger et al. |
| 6,004,291 A | 12/1999 | Ressemann et al. |
| 6,027,486 A | 2/2000 | Crocker et al. |
| 6,029,671 A | 2/2000 | Stevens et al. |
| 6,030,405 A | 2/2000 | Zarbatany et al. |
| 6,036,715 A | 3/2000 | Yock et al. |
| 6,050,972 A | 4/2000 | Zadno et al. |
| 6,059,748 A | 5/2000 | Teirstein et al. |
| 6,066,114 A | 5/2000 | Goodin et al. |
| 6,090,126 A | 7/2000 | Burns et al. |
| 6,096,009 A | 8/2000 | Windheuser et al. |
| 6,129,700 A | 10/2000 | Fitz et al. |
| 6,129,708 A | 10/2000 | Enger et al. |
| 6,165,197 A | 12/2000 | Yock et al. |
| 6,179,810 B1 | 1/2001 | Wantink et al. |
| 6,190,358 B1 | 2/2001 | Fitzmaurice et al. |
| 6,190,393 B1 | 2/2001 | Bevier et al. |
| 6,231,543 B1 * | 5/2001 | Hegde et al. ............... 604/96.01 |
| 6,231,588 B1 | 5/2001 | Zadno-Azizi |
| 6,248,092 B1 * | 6/2001 | Miraki et al. ............. 604/96.01 |
| 6,273,879 B1 | 8/2001 | Keith et al. |
| 6,319,229 B1 | 11/2001 | Kim et al. |
| 6,322,577 B1 | 11/2001 | McInnes |
| 6,325,778 B1 | 12/2001 | Zadno-Azizi et al. |
| 6,331,176 B1 | 12/2001 | Becker et al. |
| 6,346,093 B1 * | 2/2002 | Allman et al. ........... 604/167.06 |
| 6,355,014 B1 | 3/2002 | Zadno-Azizi et al. |
| 6,361,529 B1 | 3/2002 | Goodin et al. |
| 6,364,894 B1 | 4/2002 | Healy et al. |
| 6,371,940 B1 | 4/2002 | Valencia et al. |
| 6,409,863 B1 * | 6/2002 | Williams et al. ............... 156/198 |
| 6,432,091 B1 | 8/2002 | Davey |
| 6,451,043 B1 | 9/2002 | McInnes et al. |
| 6,471,672 B1 | 10/2002 | Brown et al. |
| 6,488,674 B2 | 12/2002 | Becker et al. |
| 6,500,147 B2 | 12/2002 | Omaleki et al. |
| 6,517,515 B1 | 2/2003 | Eidenschink |
| 6,520,951 B1 | 2/2003 | Carrillo, Jr. et al. |
| 6,527,741 B1 | 3/2003 | Lee et al. |
| 6,540,719 B2 | 4/2003 | Bigus et al. |
| 6,554,795 B2 | 4/2003 | Bagaoisan et al. |
| 6,558,401 B1 | 5/2003 | Azizi |
| 6,575,960 B2 | 6/2003 | Becker et al. |
| 6,575,993 B1 | 6/2003 | Yock |
| 6,589,207 B1 | 7/2003 | El-Nounou |
| 6,589,226 B1 | 7/2003 | Owens |
| 6,605,057 B2 | 8/2003 | Fitzmaurice et al. |
| 6,613,075 B1 | 9/2003 | Healy et al. |
| 6,635,027 B1 | 10/2003 | Cragg et al. |
| 6,638,243 B2 | 10/2003 | Kupiecki |
| 6,656,153 B1 | 12/2003 | Sakai et al. |
| 6,685,721 B1 | 2/2004 | Kramer |
| 6,730,107 B2 | 5/2004 | Kelley et al. |
| 8,414,527 B2 * | 4/2013 | Mallaby ................... 604/103.04 |
| 2003/0040769 A1 | 2/2003 | Kelley et al. |
| 2004/0092869 A1 | 5/2004 | Venturelli |

OTHER PUBLICATIONS

U.S. Appl. No. 10/945,578, filed Sep. 9, 2004.

* cited by examiner

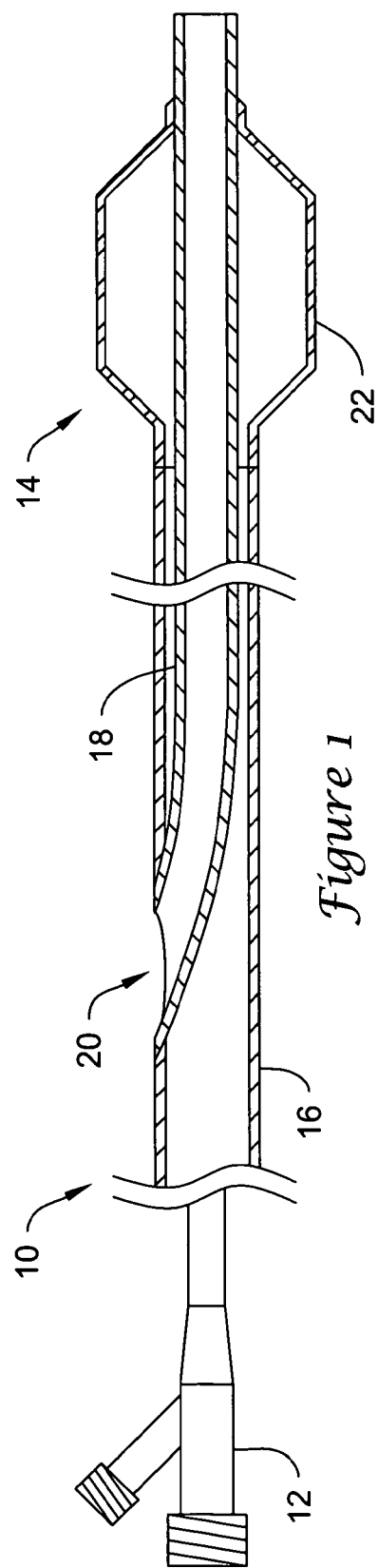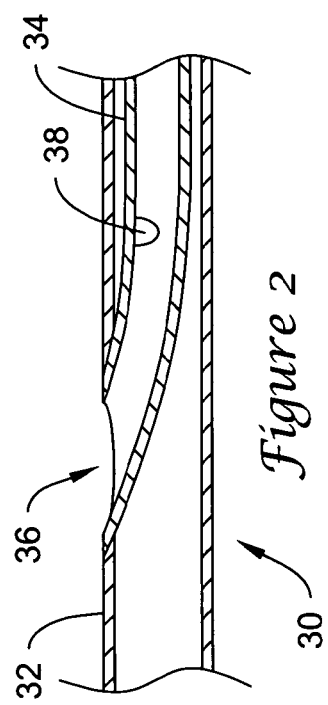

RAPID EXCHANGE CATHETERS HAVING A SEALED GUIDEWIRE LUMEN AND METHODS OF MAKING THE SAME

CROSS REFERENCE TO RELATED APPLICATIONS

This application is a continuation of U.S. patent application Ser. No. 10/945,578, filed Sep. 21, 2004 (pending), the entire disclosure of which is incorporated herein by reference.

FIELD OF THE INVENTION

The present invention is related to the field of medical devices. More particularly, the present invention is related to rapid exchange catheter technologies.

BACKGROUND OF THE INVENTION

Catheters are used in a variety of minimally invasive medical procedures. A major portion of the catheter field involves catheters that track over a guidewire, such as angioplasty catheters that are used to advance an inflatable member over a guidewire to a desired vascular location. One advancement in this field has been the use of rapid exchange catheters in place of standard over-the-wire catheters.

A standard over-the-wire catheter typically tracks over a guidewire over its entire length such that, in order to maintain a distal guidewire location while exchanging the catheter, a guidewire extension or very long guidewire is used. To exchange the standard over-the-wire catheter, the guidewire is held in place while the catheter is withdrawn. The proximal end of the guidewire is held until the distal end of the catheter exits the patient's body, while the distal end of the guidewire remains in the desired location, meaning that the guidewire, during exchange, must be twice as long as the catheter.

A rapid exchange catheter tracks over the guidewire for only a short distal portion of the catheter. Examples of rapid exchange catheters, their use, and methods for making such catheters are illustrated by Williams et al. in U.S. Pat. No. 6,409,863, the disclosure of which is incorporated herein by reference. The catheter shown by Williams et al. includes an outer member and a distally located inner member, with a balloon proximal end attached to the distal end of the outer member and a balloon distal end attached to the distal inner member. A proximal guidewire port is located distal of the proximal end of the catheter, with the distal inner member opening at its proximal end to the proximal guidewire port, and extending to the distal end of the catheter.

One difficulty which can arise with some rapid exchange catheters is that an inner member defining the distal guidewire lumen may allow passage of fluid therethrough. Because the proximal guidewire port is typically in view of fluoroscopic instruments, passage of contrast fluid used to visualize the treatment location (for example, the location of a lesion in a blood vessel) proximally through the guidewire lumen can be misinterpreted as indicating device failure during inflation of a distally located balloon. Reducing the diameter of the guidewire lumen to prevent fluid passage, however, can make it more difficult to push the catheter over the guidewire. Reducing the slidability of the catheter with respect to the guidewire (and vice-versa) can make it more difficult to maintain and manipulate guidewire position, thereby making the physician's task of advancing a catheter over the guidewire more difficult.

SUMMARY OF THE INVENTION

The present invention, in an illustrative embodiment, includes a rapid exchange catheter having an outer member and an inner member defining a guidewire lumen, with the outer member including a proximal guidewire port located distally of the proximal end of the catheter. The inner member extends from the proximal guidewire port to the distal end of the catheter. The inner member includes a fluid stop portion (less than its total length) configured to prevent fluid flow therethrough when a guidewire is disposed through the inner member. In several embodiments, the fluid stop portion is disposed proximal the distal end of the inner member. In one such embodiment, a seal is disposed within the inner member. In another such embodiment, the inner member includes a necked portion proximal its distal end.

The present invention, in additional illustrative embodiments, includes methods of making a rapid exchange catheter having an inner member adapted to receive a guidewire. The inner member is further adapted to prevent fluid flow therethrough when a guidewire is disposed through the inner member. In one such embodiment, a seal is placed in the inner member. In another embodiment, a portion of the inner member is subjected to pressure and heat while disposed over a mandrel having a tapered or necked portion, such that a portion of the inner member necks down to a narrowed diameter for a length less than the total length of the inner member.

BRIEF DESCRIPTION OF THE DRAWINGS

FIG. 1 shows a portion of a rapid exchange type catheter in cross section;

FIG. 2 shows, in partial cross section, an illustrative rapid exchange catheter proximal guidewire port and proximal portion of a guidewire lumen having a fluid blocking means;

DETAILED DESCRIPTION OF THE PREFERRED EMBODIMENTS

Figure 3:
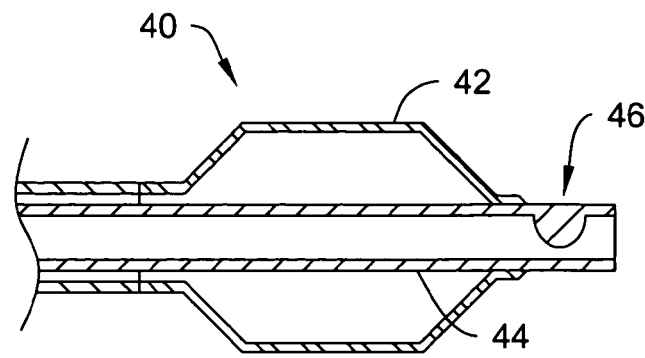
FIG. 3 shows, in partial cross section, an illustrative distal portion of a guidewire lumen for a rapid exchange catheter having a fluid blocking means.

The following detailed description should be read with reference to the drawings. The drawings, which are not necessarily to scale, depict illustrative embodiments and are not intended to limit the scope of the invention.

As used herein, the term "rapid exchange" should be understood as imparting the same or similar meanings as other terms used in the catheter arts such as single operator exchange. In particular, "rapid exchange catheter" includes any catheter designed to enable exchange of a catheter placed using a guidewire without requiring a guidewire extension or guidewire that is substantially longer than the catheter itself. While much of the following description and several of the figures illustrate balloon catheters, other catheter types may incorporate the improvements herein, including, for example, fluid infusion cannulas, cutting instruments, non-balloon self-expanding stent delivery catheters, and/or atherectomy devices. Vascular and non-vascular (such as biliary or uretogenital) uses are contemplated.

FIG. 1 illustrates relevant features of a rapid exchange catheter 10. The catheter 10 includes a proximal end 12 and a distal end 14. An outer tubular member 16 defines an inflation lumen, and an inner tubular member 18 defines a guidewire lumen from a guidewire port 20 to the distal end 14 of the catheter 10. The proximal end of a balloon 22 is secured to the distal end of the outer tubular member 16. The distal end of the balloon 22 is secured near the distal end of the inner tubular member 18. While shown as a butt-joint, the balloon 22 is often bonded to the outer tubular member 16 by a process performed on an overlap of the two. The balloon 22 may be secured by any suitable manner, for example, using heat or welding methods, or by the use of an adhesive. The outer tubular member 16 includes a proximal portion extending from the proximal end 12 to the guidewire port 20 and a distal portion extending from the guidewire port 20 to the balloon 22.

A number of designs for and additional features of a rapid exchange catheter 10 have been developed. For example, the outer tubular member 16 may be made up of several tubes connected to one another including hypotubes, polymeric tubes, and/or reinforced polymeric tubes. The balloon 22 may be inelastic or elastic. Rather than a side exit as shown in FIG. 1, the guidewire port 20 may face a generally axial direction. Core wires, transition support elements, and the like may also be provided. A number of radiopaque markers may be provided at various locations, as desired. The inclusion or addition of any of these features should be understood as being optional features of the following illustrative embodiments of the present invention. Furthermore, the exact location and manner of securement/attachment between the various elements can vary widely as further optional features of the following illustrative embodiments. Finally, the materials used are also a matter of design choice and may vary widely within the scope of the present invention.

FIG. 2 illustrates in cross section a guidewire port 36. The catheter 30 is illustrated having an outer member 32 and an inner member 34. During use, a difficulty which can arise is the backflow of contrast fluid from the distal end (not shown) of the catheter 30 through the inner member 34 (which defines a guidewire lumen) to the guidewire port 36. The contrast fluid can then exit the catheter shaft and can appear, under fluoroscopy, to indicate catheter failure due to a leak at the guidewire port 36.

For example, a radiopaque fluid or saline including a radiopaque material may be used to inflate a balloon disposed on the distal end of the catheter 30. If radiopaque fluid was previously used to visualize the area of treatment at the distal end of the catheter, it may (unless prevented from doing so) flow up the inner member 34 to the guidewire port 36, and exit the catheter 30 there. If this occurs, it can appear as though the inflation fluid were leaking at the guidewire port 36. Observation of the fluid exiting at the guidewire port 36 can unnecessarily cause a practitioner to believe that the inflation lumen is leaking, halt the procedure, and remove and discard the catheter 30. This is costly in terms of practitioner and procedure time, materials and products, and, most importantly, patient discomfort and stress.

To prevent such leakage or flow through the inner member 34, the illustrative catheter 30 is provided with a fluid stop structure 38, illustrated as a narrowing or bump in the lumen defined by the inner member 34. The fluid stop structure 38 may be a deposited material or an inserted piece of material such as a plastic, wax, leather, foam, rubber, artificial rubber, or any flexible material that can prevent fluid flow through the inner member while a guidewire is disposed therein. Preferably the fluid stop structure 38 is designed, coated, or otherwise constructed to avoid creating undue friction with a guidewire (not shown) passing therethrough. By including the fluid stop structure 38, radiopaque fluid is prevented or substantially prevented from exiting the catheter at the guidewire port 36.

FIG. 3 illustrates an alternative sealing structure. In FIG. 3, a catheter 40 with balloon 42 and inner member 44 includes a sealing structure shown as seal 46 disposed near the distal end of the guidewire lumen. The seal 46 may be, for example, a seal material or seal itself secured inside of the inner member 44. Alternatively, the inner member 44 may be provided as including an internal lumen irregularity that functions as a seal 46 to prevent fluid flow through the inner member 44 when a guidewire (not shown) is disposed therein. By moving the seal 46 away from the distal tip of the catheter 40, it becomes easier to backload a catheter over a guidewire (loading by inserting the proximal end of the guidewire into the distal end of the catheter 40 and advancing the catheter 40 over the guidewire).

Figure 4:
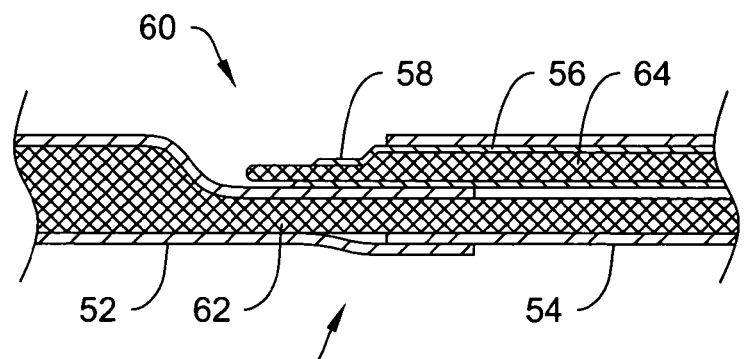
FIG. 4 shows, in partial cross section, mandrels and tubular members configured for a step in constructing a rapid exchange catheter with fluid blocking means in a proximal portion of the distal guidewire lumen.

FIG. 4 illustrates a step in a process of making a rapid exchange type catheter having a fluid blocking feature in its distal inner member. In particular, the catheter 50 is shown having integral parts including a proximal member 52, a distal outer member 54, and a distal inner member 56. The proximal end 58 of the distal inner member 56 is shown as fitting onto a reduced size portion of a distal mandrel 64. A proximal mandrel 62 passes through the proximal member 52 past a guidewire port 60.

Several designs may be used for the proximal end 58 of the distal inner member 56. The proximal end 58 of the distal inner member 56 may be formed as a tapered portion. Alternatively, the distal inner member 56 may be a simple tubular member, with a triangular portion cut from its proximal end 58 to allow the distal inner member 56 to be compressed around the distal mandrel 64. In a preferred embodiment, the distal inner member 56 is a tubular member that is shaped over the distal mandrel 64 during a heat-welding step in which the proximal member 52 is attached to the distal outer member 54 and distal inner member 56 to form the port joint or guidewire port 60. To achieve such a structure, the proximal mandrel 62 may include a distal end having a crescent or half-moon transverse cross-sectional shape such that it can partially surround the distal inner member 56. In at least one embodiment, the proximal end 58 of the distal inner member 56 is sized to allow relatively easy passage of a guidewire therethrough, while preventing undesired fluid flow.

One advantage of the embodiment of FIG. 4 is that it can be even easier to introduce a guidewire to the distal end (not shown) of the catheter than with the embodiment in FIG. 3. This is due to the fact that the narrowed portion of the inner members (44, 56) is the location at which the greatest friction will likely occur when a guidewire is advanced or withdrawn. By placing the fluid restricting feature away from the distal end of the catheter, it becomes possible to advance the guidewire through a portion of the inner member before reaching this friction-creating point. Further, the opening at the distal end becomes bigger, and the inner/outer members may provide column strength for easing passage of the guidewire without buckling either the catheter or the guidewire.

For example, in several rapid exchange embodiments, the method of introduction over a guidewire includes back-loading the distal end of the catheter over the proximal end of a guidewire. This method can be difficult using, for example, a structure as shown by Fitzmaurice et al. in U.S. Pat. No. 6,190,358, which shows necking of the guidewire member at its distal tip. The distal tip will typically be quite soft and flexible, sometimes taking the form of a "bumper" tip to avoid damaging blood vessels during advancement. Typically the proximal end of a guidewire has the greatest diameter and stiffness for the guidewire. Getting the proximal tip of the guidewire into such a delicate and soft structure without damaging the catheter can be a challenge, particularly given that the practitioner will usually be wearing gloves. Furthermore, placing the necked portion right at the distal tip may stiffen the "bumper" tip, reducing its effectiveness in preventing damage to surrounding tissue.

Figure 5:
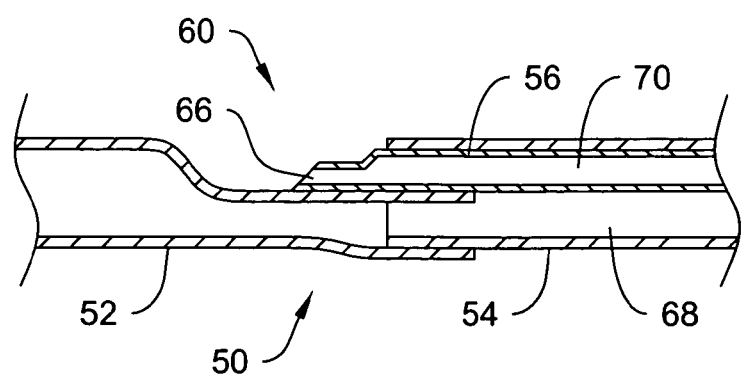
FIG. 5 shows, in partial cross section, an illustrative rapid exchange proximal guidewire port that may be constructed as shown in FIG. 4.

FIG. 5 illustrates, in section, the catheter 50 from FIG. 4 after a welding/fusing or other attachment step. It can be seen that the catheter includes a proximal member 52, distal outer member 54, and distal inner member 56. A guidewire port 60 is located at a port joint. Near the guidewire port 60 is a fluid restriction feature 66 shown as a narrowing of the guidewire lumen 70 defined by the distal inner member 56. Note that it is not necessary for the distal inner member 56 to remain in contact with the distal outer member 54 distal of the guidewire port 60, where the catheter may assume a generally coaxial/concentric configuration. The inflation lumen 68 may have a crescent shape across the port joint near the guidewire port 60, and may take an annular shape distal of the guidewire port 60, as desired. The integral parts 52, 54, 56 are shown separately for illustrative purposes. However, near the guidewire port 60 these parts will typically fuse and blend together to a certain extent.

Figure 6:
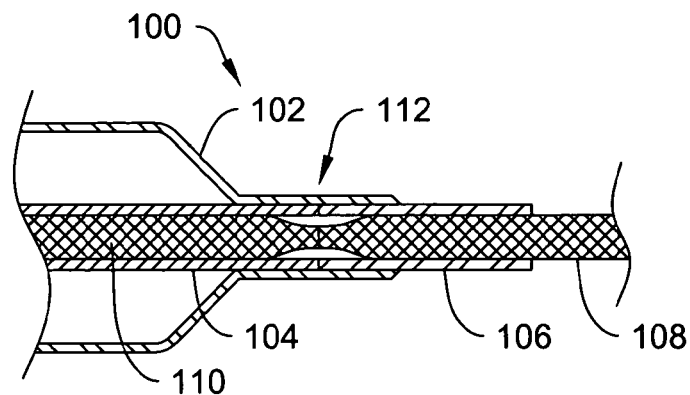
FIG. 6 shows, in partial cross section, mandrels and tubular members configured for a step in constructing an alternative rapid exchange catheter with fluid blocking means in the distal portion of the distal guidewire lumen.

FIG. 6 illustrates, in section, a method for providing a fluid blocking feature near the distal end of a rapid exchange catheter. The catheter 100 is illustrated having a balloon 102 attached at its distal end to an inner tubular member 104 and a distal bumper tip 106. The use of a very soft or atraumatic bumper tip 106 makes advancement of a catheter in a blood vessel easier by improving trackability and avoiding vessel trauma. Such softened tips may be used in other environments as well. The balloon 102 is secured by a heating process (such as a laser welding process) over the butt-joint between the inner tubular member 104 and the bumper tip 106. For the illustrative embodiment of FIG. 6, before the heating step to secure the balloon 102 to the inner tubular member 104 and the bumper tip 106, mandrels 108, 110 are passed into the bumper tip 106 and inner tubular member 104, respectively. The mandrels 108, 110 help maintain the shape and patency of the lumens for the inner tubular member and bumper tip. To provide a fluid blocking feature, the tips of one or both of the mandrels may be notched, tapered or trimmed to provide a narrowed mandrel section.

Figure 7:
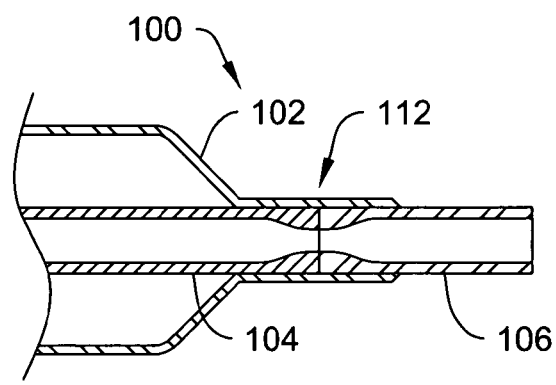
FIG. 7 shows, in partial cross section, a distal end of an illustrative rapid exchange catheter that may be constructed as shown in FIG. 6.

After the various elements shown in FIG. 6 are subjected to a heat bonding step, the mandrels 108, 110 are removed and the configuration shown in FIG. 7 is the result. In particular, the balloon 102 is secured over the inner tubular member 104 and the bumper tip 106. A fluid blocking feature 112 has been created by plastic deformation during the heating step, with one or both of the inner tubular member 104 and bumper tip 106 being deformed around the mandrels 108, 110 to create a narrowed lumen section or lip. The fluid blocking feature 112 is preferably sized to block fluid flow through the combination of the inner tubular member 104 and bumper tip 106 when a guidewire is disposed therethrough. Because the fluid blocking feature 112 is not at the distal tip of the bumper tip 106, instead being disposed proximally thereof, it may be easier to backload a guidewire (not shown) with the catheter 100.

Typically the sizing of such catheters renders the distance from the distal end for the fluid blocking feature 112 relatively long even though appearing, in terms of absolute magnitude, rather short. As an example, the bumper tip 106 in some embodiments may have a length in the range of about 2-4 mm. A fluid blocking feature as shown in FIGS. 6-7 would, therefore, be in the range of 2-4 mm from the distal end of the catheter. As such, the distal opening of the inner member may be large enough to facilitate back-loading of a guidewire therein, with the changing diameter of the guidewire lumen guiding the guidewire past the fluid blocking structure.

Figure 8:
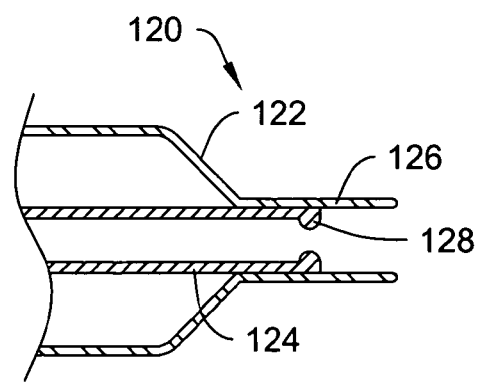
FIG. 8 shows, in partial cross section, another distal end for an illustrative rapid exchange catheter; and, FIGS. 9A-9B illustrate, in schematic section views, a rapid exchange proximal guidewire port before and after a port molding method of the present invention.

FIG. 8 shows, in partial cross section, another distal end for an illustrative rapid exchange catheter. The catheter 120 includes a balloon 122, an inner member 124, and a bumper tip 126. In the illustrative embodiment, the balloon 122 and bumper tip 126 form a butt-joint over the inner member 124. These three elements may be secured to one another by placing mandrels therethrough and subjecting the joint(s) to heat. By using mandrels having a stepped or tapered portion, a fluid blocking structure 128 may be formed at the distal end of the inner member 124. In the illustration, the fluid blocking structure 128 is formed using material from the distal end of the inner member 124. Such a formation may optionally be further facilitated by the use of materials for the three elements shown 122, 124, 126 such that the inner member 124 flows more readily at a given temperature than the balloon 122 or bumper tip 124.

A number of molded port joints and subassemblies are illustrated in copending application Ser. No. 10/653,375, filed Sep. 2, 2003 and entitled CATHETER INCLUDING A UNIBODY DISTAL GUIDEWIRE PORT AND METHOD OF MANUFACTURE, the disclosure of which is incorporated herein by reference. Modification of the mandrels illustrated therein may be performed in accordance with the present invention to provide fluid flow stops in the guidewire lumens of embodiments therein.

Figure 9A:
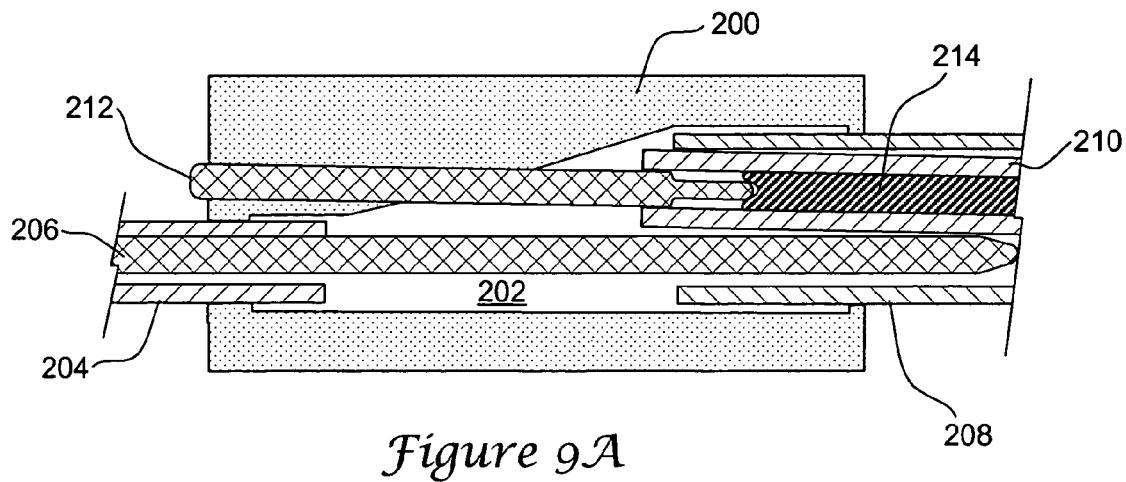
Figure 9B:
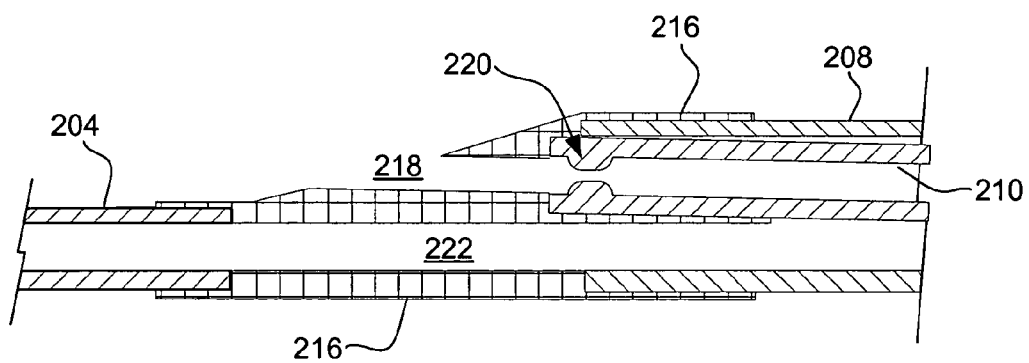

For example, FIGS. 9A-9B illustrate, in schematic section views, mandrels and tubular members disposed prior to performing a molding step to construct an insert molded port joint, and the port joint once so created. As illustrated in FIG. 9A, a port mold 200 is provided defining a molding volume 202. A proximal member 204 is partly inserted to the port mold with a mandrel 206 extending distally therefrom. The mandrel 206 extends through the molding volume 202 into a space between the distal outer member 208 and distal inner member 210. The mandrel 206 may include a proximal round section and a distal section having a taper or that is crescent shaped to fit in the space between the distal inner member 210 and distal outer member 208.

A first guidewire mandrel 212 is provided extending from the port mold 200 into the distal inner member 210. As can be seen, the end of the first guidewire mandrel 212 includes a portion of reduced diameter. A second guidewire mandrel 214 extends through the distal inner member 210 from its distal end near the proximal end of the distal inner member 210. The second guidewire mandrel 214 may be shaped at its end to partially mate with the first guidewire mandrel 212, as shown. However, there is a region where the first guidewire mandrel 212 has a lesser diameter than that of the distal inner member 210 without the second guidewire mandrel 214 extending thereto.

An injectate material is then forced into the port mold 200. The injectate material will be typically hot, and will provide pressure as well. The combination of heat and pressure then causes the members 204, 208, 210 to be secured together. As shown in FIG. 9B, when the injection/heating/pressure step is completed, the members 204, 208, 210 are secured to one another either directly or via the injected material 216, which surrounds and adheres to each member 204, 208, 210. A guidewire port 218 is provided by the use of the mandrels 212, 214 (not shown). A guidewire passage includes the interior of the guidewire port 218 as well as the interior of the distal inner member 210. It can be seen that a fluid blocking feature 220 resides therein, as a result of the effects of heat and pressure on the area of the distal inner member 210 near where the smaller diameter distal end of the first guidewire mandrel 212 was. Meanwhile, an inflation lumen 222 has been maintained going through the port joint itself from the inner member 204 to the lumen between the distal inner member 210 and the distal outer member 208.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A catheter comprising:
    a catheter shaft including a proximal end and a distal end, the catheter shaft including;
        an outer tubular member including a proximal end and a distal end;
        an inner member including a proximal end and a distal end and defining a lumen, the inner member disposed at least partially within the outer member;
        an inflation lumen disposed within the outer tubular member and adjacent the inner member; and
        a guidewire port that opens into the lumen of the inner member, the guidewire port being located at a position along the shaft that is distal of the proximal end of the shaft;
        the inner member including a fluid restriction feature defined by a reduction in a diameter of the lumen of the inner member, the fluid restriction feature being located in a proximal portion of the inner member.

2. The catheter according to claim 1, wherein the proximal portion of the inner member including the fluid restriction feature extends beyond the proximal end of the outer tubular member.

3. The catheter according to claim 1, wherein the proximal end of the inner member is located proximal to the proximal end of the outer tubular member.

4. The catheter according to claim 1, wherein the proximal end of the inner member is located adjacent to the proximal end of the outer tubular member.

5. The catheter according to claim 1, wherein the proximal end of the inner member is located at a position between the proximal end and the distal end of the outer tubular member.

6. The catheter according to claim 1, wherein the reduction in diameter of the lumen is defined by a reduction in an inner diameter of the inner member.

7. The catheter according to claim 1, wherein the fluid restriction feature comprises a region of increased wall thickness that defines the reduction in diameter of the lumen.

8. The catheter according to claim 1, wherein the fluid restriction feature comprises a coating on an inner surface of the inner member to facilitate passage of a guidewire through the lumen of the inner member.

9. The catheter according to claim 1, wherein the outer member defines a second lumen, the second lumen including a portion disposed between the inner member and the outer member, wherein the inner member prevents fluid flow from the second lumen into the lumen of the inner member.

10. The catheter according to claim 1, wherein the guidewire port is located at a proximal end of the inner member.

11. The catheter according to claim 10, wherein the guidewire port is located distal to the proximal end of the outer tubular member.

12. The catheter according to claim 10, wherein the guidewire port is located proximal to the proximal end of the outer tubular member.

13. The catheter according to claim 10, wherein the guidewire port is located adjacent to the proximal end of the outer tubular member.

14. A catheter comprising:
    an elongated catheter body including a proximal end and a distal end, the elongated catheter body including;
        an outer tubular member including a proximal end and a distal end;
        an inner tubular member at least partially disposed within the outer tubular member, the inner tubular member comprising a first portion having a first inner diameter and at least a second portion comprising a second inner diameter wherein the first inner diameter is less than the second inner diameter and wherein the first portion of the inner tubular member is located proximal to the distal end of the inner tubular member;
        an inflation lumen disposed within the outer tubular member and adjacent the inner member; and
        a guidewire port in fluid communication with the first portion of inner tubular member, the guidewire port located at a proximal end of the inner tubular member.

15. The catheter according to claim 14, wherein the first portion of the inner tubular member comprises an increased wall thickness relative to a wall thickness of the second portion, wherein the increased wall thickness defines the first inner diameter.

16. The catheter according to claim 14, wherein the first portion of the inner tubular member further comprises a reduced outer diameter.

17. The catheter according to claim 14, wherein the first portion of the inner tubular member is located proximal to the proximal end of the outer tubular member.

18. The catheter according to claim 14, wherein the proximal end of the inner tubular member is located a position between the proximal end and the distal end of the outer tubular member.

* * * * *